(12) United States Patent
Ferguson et al.

(10) Patent No.: US 8,835,380 B2
(45) Date of Patent: Sep. 16, 2014

(54) THERAPEUTIC CONJUGATES

(75) Inventors: Elaine Ferguson, Cardiff (GB); David Thomas, Cardiff (GB); Timothy Walsh, Cardiff (GB)

(73) Assignee: University College Cardiff Consultants Limited, Cardiff (GB)

(*) Notice: Subject to any disclaimer, the term of this patent is extended or adjusted under 35 U.S.C. 154(b) by 82 days.

(21) Appl. No.: 13/805,888

(22) PCT Filed: Jun. 1, 2011

(86) PCT No.: PCT/GB2011/051029
§ 371 (c)(1),
(2), (4) Date: Dec. 20, 2012

(87) PCT Pub. No.: WO2012/035310
PCT Pub. Date: Mar. 22, 2012

(65) Prior Publication Data
US 2013/0096049 A1    Apr. 18, 2013

(30) Foreign Application Priority Data

Jun. 23, 2010 (GB) .................................. 1010500.5

(51) Int. Cl.
*A61K 45/06* (2006.01)
*A61K 47/48* (2006.01)

(52) U.S. Cl.
CPC ............. *A61K 47/4823* (2013.01); *A61K 45/06* (2013.01)
USPC ............... 514/1.4; 530/322; 514/2.3; 514/2.8

(58) Field of Classification Search
None
See application file for complete search history.

(56) References Cited

U.S. PATENT DOCUMENTS

2010/0016546 A1   1/2010   Bishop

FOREIGN PATENT DOCUMENTS

WO    2010080819 A1    7/2010
WO    WO 2010080819 A1 *  7/2010

OTHER PUBLICATIONS

Angelova et al. J Colloid and Interface Science. 212;275-279:1999.*
Falagas et al. Critical Care. 10;1-13:2006.*
Duncan et al. Biomacromolecules. 9;1146-1154:2008.*
Ruth Duncan, et al.; "Polymer Masked—Unmasked Protein Therapy. 1. Bioresponsive Dextrin—Trypsin and—Melanocyte Stimulating Hormone Conjugates Designed for a-Amylase Activation"; Biomacromolecules 2008, vol. 9, pp. 1146-1154.
Dale Hreczuk-Hirst, et al.; "Dextrins as potential carriers for drug targeting: tailored rates of dextrin degradation by introduction of pendant groups"; International Journal of Pharmaceutics, vol. 230, (2001), pp. 57-66.
International Search Report and Written Opinion for International application No. PCT/GB2010/051029 dated May 3, 2012.
Ruth Duncan, et al.; "Polymer Masked—Unmasked Protein Therapy. 1. Bioresponsive Dextrin—Trypsin and—Melanocyte Stimulating Hormone Conjugates Designed for a—Amylase Activation"; Biomacromolecules 2008, vol. 9, pp. 1146-1154.
Jian Li, et al.; "Pharmacokinetics of colistin methanesulphonate and colistin in rats following an intravenous dose of colistin methanesulphonate"; Journal of Antimicrobial Chemotherapy (Mar. 2004), vol. 53, No. 5, pp. 837-840.
Lin Bi, et al.; "Designing carbohydrate nanoparticles for prolonged efficacy of antimicrobial peptide"; Journal of Controlled Release (2011), vol. 150., No. 2, pp. 150-156.

* cited by examiner

*Primary Examiner* — Karlheinz R Skowronek
*Assistant Examiner* — Schuyler Milton
(74) *Attorney, Agent, or Firm* — King & Schickli, PLLC

(57) ABSTRACT

The invention concerns a novel antimicrobial peptide (AMP) polymer conjugate comprising at least one AMP, typically colistin, and a dextrin polymer wherein said dextrin polymer has a molecular weight between 5,000-60,000 g/mol and is modified by the additions of pendant groups which increase the stability of the conjugate and so delays its degradation thereby slowing the rate at which the AMP is released.

17 Claims, 16 Drawing Sheets

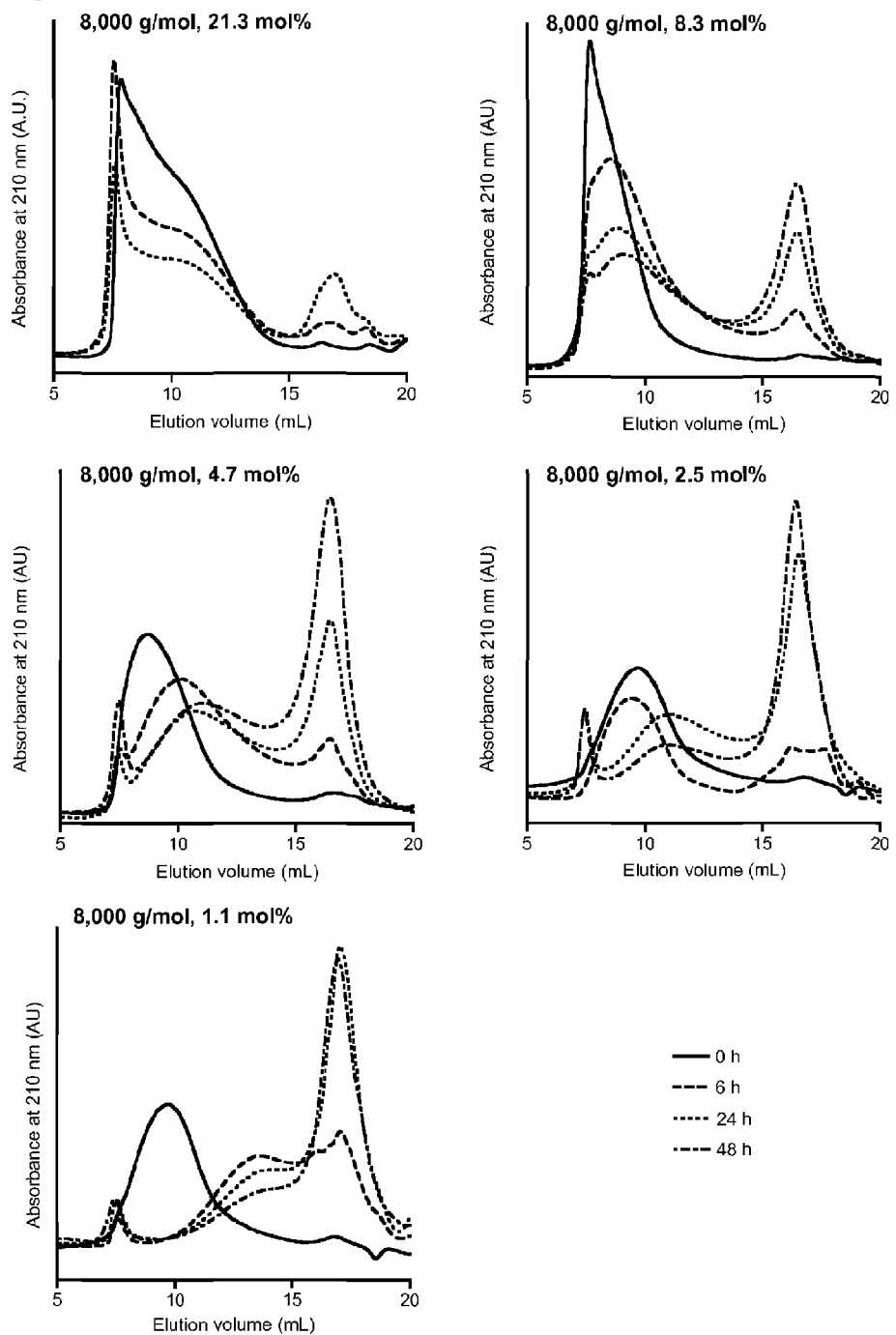

|  | IC$_{50}$ (μg/mL colistin eq.) | IC$_{50}$ (μg/mL S. dextrin eq.) |
|---|---|---|
| Colistin | 20 | - |
| CMS | 25 | - |
| Succinoylated dextrin | - | 4,200 |
| Dextrin-colistin (1.1 mol%) | 90 | 650 |
| Dextrin-colistin + amylase | 60 | 400 |

THERAPEUTIC CONJUGATES

This application is the national stage of international patent application no. PCT/GB2011/051029 filed on Jun. 1, 2011, which in turn claims priority from British Patent Application Serial No. GB 1010500.5 filed on Jun. 23, 2010, the disclosures of each of which are incorporated herein by reference in their entirety.

The invention relates to a novel drug conjugate comprising an antimicrobial peptide and a biodegradable polymer; a pharmaceutical composition comprising said conjugate; a combination therapeutic comprising said conjugate and/or said composition and at least one other therapeutic; a method of treatment using said conjugate, said composition or said combination therapeutic; and a method for the manufacture of said conjugate, said composition or said combination therapeutic.

INTRODUCTION

Bacterial resistance to antibiotic therapy is a major world health problem. Unfortunately, decreases in the design and development of new antibiotic entities have been mirrored by increased microbial resistance to currently available antibiotics. Further, the prevalence of infections by Gram-negative, multi-drug resistant organisms is rising annually.

Examples of Gram-negative bacteria include *Escherichia coli, Staphylococcus aureus, Salmonella, Shigella*, and other Enterobacteriaceae. Other medically relevant Gram-negative cocci include *Neisseria gonorrhoeae* which causes sexually transmitted disease, *Neisseria meningitidis* which causes meningitis, and *Moraxella catarrhalis* which causes respiratory symptoms. Medically relevant Gram-negative bacilli include *Hemophilus influenzae, Klebsiella pneumoniae, Legionella pneumophila, Pseudomonas aeruginosa*, which primarily cause respiratory problems, *Escherichia coli, Proteus mirabilis, Enterobacter cloacae, Providencia stuartii, Serratia marcescens* which primarily cause urinary problems and *Helicobacter pylori, Salmonella enteritidis, Salmonella typhi* which primarily cause gastrointestinal problems. Gram-negative bacteria associated with nosocomial infections include *Acinetobacter baumannii, Acinetobacter haemolyticus, Acinetobacter iwoffi* which cause bacteremia, secondary meningitis, and ventilator-associated pneumonia in intensive care units of hospital establishments.

To elaborate on just one example, the Gram-negative, opportunistic pathogen *Pseudomonas aeruginosa* is a major clinical problem particularly, but not exclusively, in patients with cystic fibrosis, burns and skin wounds. Moreover, β-lactam, aminoglycoside and fluoroquinolone resistance is common in this organism.

The need to combat microbial infections has led clinicians to use antimicrobials which are effective against Gram-negative organisms but which are also known to have toxicity issues (e.g. colistin and polymyxin B). In practise, this means the effective utilisation of these agents is undesirable and severely limited.

Colistin is a cationic anti-microbial peptide (AMP) which is highly active againsts multidrug-resistant Gram-negative bacteria. However, this AMP is not readily absorbed orally and the free drug is known to be particularly nephro- and neurotoxic. Consequently, its clinical use is limited. Typically, it is administered intravenously as colistin methanesulfonate (CMS). Although sulfomethylation decreases the in vitro antibacterial potency of colistin, advantageously, the toxicity and undesirable side effects of colistin are reduced. CMS is therefore, essentially, a pro-drug that is readily hydrolysed to partially sulfomethylated derivatives and colistin in aqueous solution (FIG. 1). However, this hydrolysis is uncontrolled, and may even occur before administration to the patient-leading to reported deaths. It follows that a safe, effective delivery system for this AMP would revolutionise the treatment of patients with Gram-negative infections and increase the safe use of the AMP where currently no alternative exists.

We have developed a novel nanomedicine-based delivery system to target the delivery of colistin, as a model AMP, to sites of infection thereby increasing bioactivity and bioavailability whilst decreasing systemic toxicity and improving clinical effectiveness.

STATEMENTS OF INVENTION

According to a first aspect of the invention there is provided an anti-microbial peptide (AMP) polymer conjugate comprising at least one AMP and a dextrin polymer wherein said dextrin polymer has a molecular weight between 5,000-60,000 g/mol and is modified by the addition of pendant groups which increase the stability of the conjugate and so delays dextrin degradation thereby slowing the rate at which the AMP is released.

We consider that low molecular weight dextrins such as $10,000\pm5,000$ g/mol (5, 6, 7, 8, 9, 10, 11, 12, 13, 14 or $15\times10^3$ g/mol) are useful for treating acute infections where relatively fast release of AMP is desired such as release of 50% of AMP within 24 h. Ideally the dextrin has a molecular weight of 8,000 g/mol.

Alternatively, large molecular weight dextrins such as $50,000\pm10,000$ g/mol (40, 41, 42, 43, 44, 45, 46, 47, 48, 49, 50, 51, 52, 53, 54, 55, 56, 57, 58, 59 or $60\times10^3$ g/mol) are useful for treating chronic infections where relatively slow release of AMP is desired such as release of 50% of AMP within 72 h. For example when treating cystic fibrosis. Ideally the dextrin has a molecular weight of 51,000 g/mol.

We have advantageously discovered that conjugation of dextrin polymer to an AMP could, not only limit systemic toxicity, but passively target the AMP to sites of inflammation by, we believe, the 'Enhanced Permeability and Retention (EPR) effect' seen in inflammation and cancer. The EPR effect is the property by which certain sized molecules, typically macromolecular drugs, tend to accumulate in inflamed, diseased tissues much more than in normal healthy tissue. The general explanation that is given for this phenomenon is the increased blood flow and vascular permeability at diseased sites.

In a preferred embodiment of the invention the AMP is colistin, most ideally, in its free drug form. Indeed, we have discovered that conjugation of colistin to the dextrin polymer enables us to use the free drug form of colistin instead of CMS. This is because the polymer effectively masks the AMP during the process of its passive targeting and so overcomes any otherwise deleterious toxicity problems. Moreover, use of the free drug form is further advantageous because it makes the production of the conjugate simpler. In a preferred embodiment of the invention the dextrin-colistin conjugates typically contain ~3 amide bonds per colistin molecule, more specifically 1-4 bonds per colistin molecule and yet more specifically 0.97-3.54 bonds per colistin molecule.

More preferably the molar ratio of dextrin to colistin is between 1:0.6 and 1:1.8 as shown in Table 2. Preferably, 1:0.6 or 1:0.7 or 1:1 or 1:1.2 or 1:1.3 or 1:1.4 or 1:1.5 or 1:1.6 or 1:1.8

Those skilled in the art will appreciate that dextrin is a product of starch hydrolysis. It is a glucose polymer consisting of a number of different chain lengths. As a result an average is used to define its molecular weight, such as the weight average molecular weight Mw; or the number average molecular weight Mn. In the above invention the weight average molecular weight is used to refer to the size of the dextrin MW range.

Advantageously, dextrin is completely biodegradable and FDA approved for systemic use.

In a preferred embodiment of the invention said dextrin is modified by the addition of positively charged groups, neutral groups or negatively charged groups.

In yet a further preferred embodiment of the invention said dextrin is modified by succinoylation.

In yet a further preferred embodiment of the invention said dextrin is modified by 1-30 mol % succinoylation.

Mol % is the number of reactive groups per 100 monomers of dextrin.

More preferably said succinoylation is 0.5, 0.6, 0.7, 0.8, 0.9, 1, 1.1, 2, 2.2, 2.5, 3, 3.4, 4, 4.7, 5, 6, 6.1, 7, 8, 8.3, 9, 10, 11, 12, 13, 14, 15, 16, 17, 17.4, 18, 19, 20, 21.3, 22, 23, 24, 25, 26, 27, 28, 28.6, 29 or 30%.

According to a further aspect of the invention there is provided a pharmaceutical composition or formulation comprising the AMP polymer conjugate according to any of the above aspects or embodiments of the invention in combination with a suitable carrier.

Preferably said composition is formulated for medical or veterinary use.

The carrier, or, if more than one is present, each of the carriers, must be acceptable in the sense of being compatible with the other ingredients of the formulation and not deleterious to the recipient.

The formulation includes those suitable for oral, rectal, nasal, bronchial (inhaled), topical (including eye drops, buccal and sublingual), vaginal or parenteral (including subcutaneous, intramuscular, intraperitoneal, intravenous and intradermal) administration and may be prepared by any methods well known in the art of pharmacy.

The route of administration will depend upon the condition to be treated but preferred compositions are formulated for intravenous, parenteral, oral, nasal, bronchial or topical administration.

The composition may be prepared by bringing into association the AMP polymer conjugate of the invention and the carrier. In general, the formulations are prepared by uniformly and intimately bringing into association the conjugate with liquid carriers or finely divided solid carriers or both, and then if necessary shaping the product. The invention extends to methods for preparing a pharmaceutical composition comprising bringing a conjugate of the invention in association with a pharmaceutically or veterinarily acceptable carrier or vehicle.

Formulations for oral administration in the present invention may be presented as: discrete units such as capsules, sachets or tablets each containing a predetermined amount of the active conjugate; as a powder or granules; as a solution or a suspension of the active conjugate in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active conjugate in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored.

Other formulations suitable for oral administration include lozenges comprising the active conjugate in a flavoured base, usually sucrose and acacia or tragacanth; pastilles comprising the active conjugate in an inert base such as gelatin and glycerin, or sucrose and acacia; and mouthwashes comprising the active agent in a suitable liquid carrier.

For topical application to the skin, the conjugate may be made up into a cream, ointment, jelly, solution or suspension etc. Cream or ointment formulations that may be used for the conjugate are conventional formulations well known in the art, for example, as described in standard text books of pharmaceutics such as the British Pharmacopoeia.

Conjugates of the invention may be used for the treatment of the respiratory tract by nasal, bronchial or buccal administration of, for example, aerosols or sprays which can disperse the pharmacological active conjugate in the form of a powder or in the form of drops of a solution or suspension. Pharmaceutical compositions with powder-dispersing properties usually contain, in addition to the active conjugate, a liquid propellant with a boiling point below room temperature and, if desired, adjuncts, such as liquid or solid non-ionic or anionic surfactants and/or diluents. Pharmaceutical compositions in which the pharmacological active conjugate is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Typically, the dose of the conjugate will be determined so as to maintain the drug in the plasma or at the target site at a concentration effective to inhibit Gram-negative activity. The precise amount of a conjugate of the present invention which is therapeutically effective, and the route by which such compound is best administered, is readily determined by one of ordinary skill in the art by comparing the blood level of the conjugate or the level at the target site to the concentration required to have a therapeutic effect.

According to a yet further aspect of the invention there is provided a combination therapeutic comprising the above described conjugate, in any aspect or embodiment thereof, in combination with at least one other therapeutic.

According to a further aspect of the invention there is provided a method of treating a mammal suffering from a Gram-negative bacterial infection comprising administering to said mammal an effective amount of said conjugate or composition or combination therapeutic of the invention.

According to a further aspect of the invention there is provided a method of treating a mammal suffering from sepsis comprising administering to said mammal an effective amount of said conjugate or composition or combination therapeutic of the invention. In this aspect of the invention, we have advantageously discovered that free or unmasked colistin binds the lipopolysaccharides (LPS) characteristic of sepsis, so treating the condition. This data is shown in FIGS. 10 and 11.

LPS are characteristic components of the outer membrane of Gram-negative bacteria. LPS release can be triggered by disintegration of the bacteria, such as during cell division or antibiotic therapy. Free LPS is detected by toll-like receptor 4 (TLR4), which induces an inflammatory response and activation/secretion of pro-inflammatory cytokines. Prolonged exposure to LPS in the bloodstream leads to a systemic inflammatory response, known as sepsis, which is characterised by fever, changes in white blood cell counts, disseminated intravascular coagulation, hypotension, shock and death. Sepsis is an extremely dangerous condition, indeed, approximately 20-35% of patients with severe sepsis and 40-60% of patients with septic shock die within 30 days.

In a preferred method of the invention said conjugate, composition, or combination therapeutic is in the form of any one or more of the preferred, ideal or disclosed embodiments referred to herein.

In a further preferred method of the invention said mammal is human, equine, canine, feline, porcine, or any other domestic or agricultural species.

According to a further aspect of the invention there is provided a method for manufacturing an anti-microbial peptide (AMP) polymer conjugate comprising:
dissolving dextrin succinoylated between 1-30 mol % in a preparatory solvent;
dissolving colistin in a preparatory solvent;
adding the two solvents together and, optionally, at the same time, or subsequently, raising the pH;
allowing the reaction mixture to react; and
separating the conjugate from the reaction mixture.

In a preferred embodiment of the method said dextrin is succinoylated to the desired degree between 1-30 mol %. Ideally said dextrin preparatory solvent is distilled $H_2O$ ($dH_2O$) to which is ideally added 1-Ethyl-3-[3-dimethylaminopropyl]carbodiimide Hydrochloride (EDC), then N-hydroxysulfosuccinimide (sulfo-NHS).

Preferably said colistin preparatory solvent is $dH_2O$.

Ideally, NaOH is used to raise the pH, although other basic solutions may be used. Preferably the pH is raised to 8 or thereabouts.

Ideally, the reaction mixture is left for up to 18 h, typically 2 h. During this time the reaction mixture is ideally agitated or stirred. The conjugate is then purified from the reaction mixture ideally by FPLC, although other methods may be used such as HPLC, ion-exchange chromatography or dialysis.

Ideally, the conjugate is lyophilised and stored at −20° C.

Ideally still, said conjugate is mixed with at least one carrier and/or a further therapeutic to provide a pharmaceutical composition and/or a combination therapeutic.

In summary, we have developed a series of dextrin conjugates, typically of colistin, and characterised them to optimise diffusion, delivery and clinical effectiveness.

The rationale for this approach is that the bioresponsive dextrin-AMP conjugate will become localised at sites of inflammation/infection, following administration. The macromolecular size of the conjugate effectively delivers it to sites of inflammation/angiogenesis by the EPR effect while effectively "shielding" the peptide from the immune system and slowing renal clearance. Subsequently, slow degradation of dextrin in the inflamed, infected tissue by serum amylase releases the AMP at the target site.

We have employed dextrin as the polymeric carrier as it is used extensively clinically; being non-toxic, non-immunogenic and FDA approved. Dextrin is rapidly degraded (within minutes) by amylase to yield maltose and isomaltose, but modification by succinoylation to introduce pendant groups for conjugation decreases the amylase-mediated degradation rate and can be used to tailor the rate of peptide liberation (Hreczuk-Hirst, D., Chicco, D., German, L. & Duncan, R. Dextrins as potential carriers for drug targeting: tailored rates of dextrin degradation by introduction of pendant groups. *International Journal of Pharmaceutics* 230, 57-66 (2001), Hreczuk-Hirst, D., German, L. & Duncan, R. Dextrins as Carriers for Drug Targeting: Reproducible Succinoylation as a Means to Introduce Pendant Groups. *Journal of Bioactive and Compatible Polymers* 16, 353-365 (2001)). As a result, dextrin has the potential to be used as a partner polymer in the context of a concept named 'Polymer masked-UnMasked Protein Therapy' (PUMPT) (Duncan, R., Gilbert, H. R. P., Carbajo, R. J. & Vicent, M. J. Polymer Masked-Unmasked Protein Therapy (PUMPT) 1. Bioresponsive dextrin-trypsin and -MSH conjugates designed for α-amylase activation. *Biomacromolecules* 9, 1146-1154 (2008)). PUMPT uses conjugation of a biodegradable polymer to mask a protein or peptide's activity. Subsequent triggered degradation of the polymer regenerates bioactivity in a controlled fashion (at the target site, due to enhanced accumulation). We have found the rate of unmasking can be tailored using dextrins of different molecular weight and degree of succinoylation to optimise the pharmacokinetic/pharmacodynamic needs of the protein used.

Our conjugation and effective unmasking is controllable by chemical modification of the polymer. This allows for optimisation of drug diffusion, migration and affords the opportunity to combine bioactive agents (e.g. antimicrobial/anti-inflammatory) on individual polymer chains. Moreover we have shown that polymer-AMP conjugation reduces the neuro- and nephro-toxic side effects associated with the native colistin peptide.

Our technology there has the following advantages.
Large size of conjugate prevents access to sites of toxicity (e.g. kidney, brain)
Dextrin masks colistin from immune system and wound proteases
Potentially higher 'unmasking' rates in chronic infection sites due to higher amylase concentrations
Controlled degradation rates according to dextrin succinoylation and chain length
Unmasked colistin exerts its effect on Gram-negative bacteria and safeguards against sepsis by binding LPS In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

The invention will now be described by way of example only with reference to the following figures, wherein:—

Figure 1:
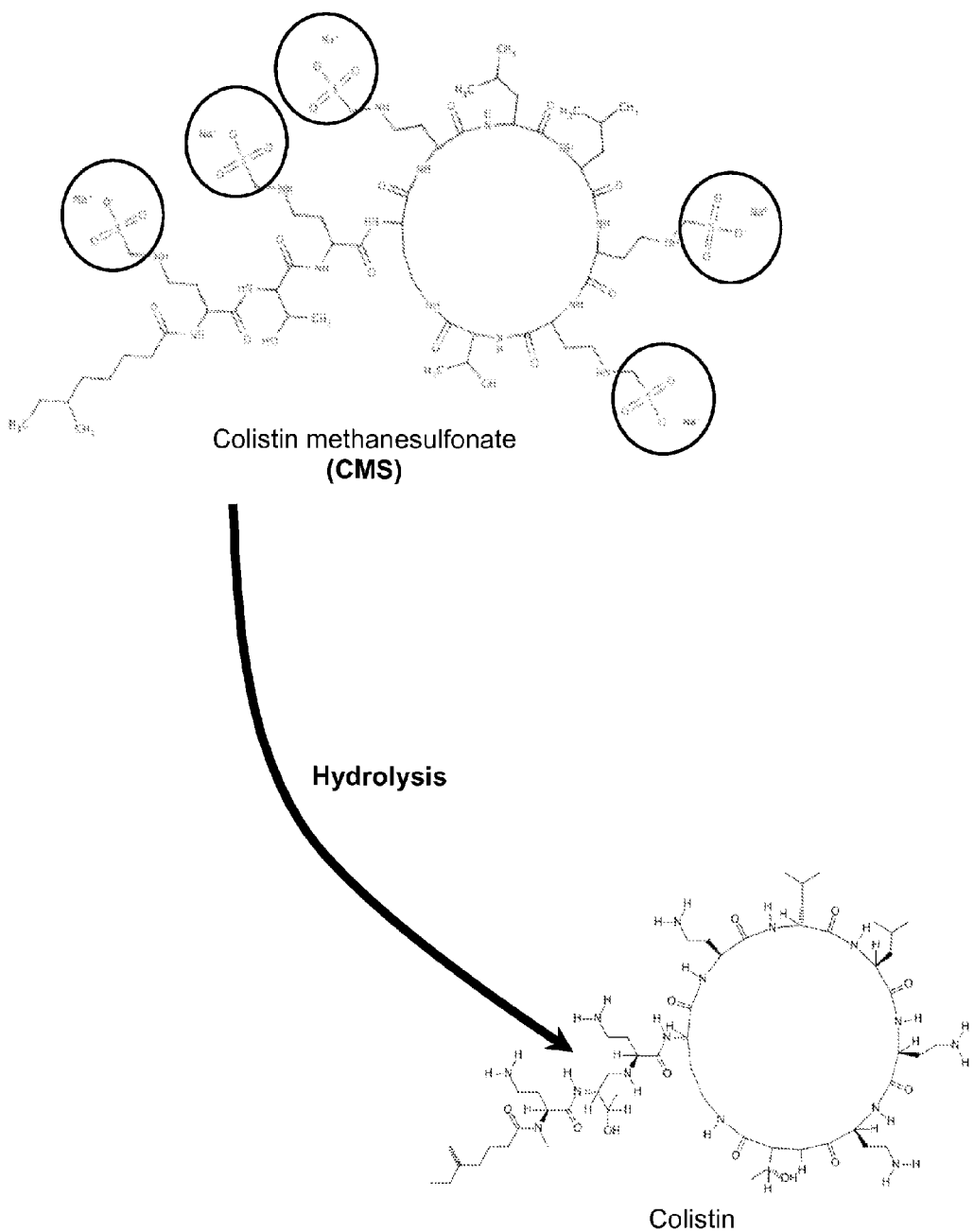
FIG. 1 depicts the hydrolysis of commercially available colistin methanesulfonate (CMS) to a variety of methanesulfonated derivatives and colistin.
Figure 2:
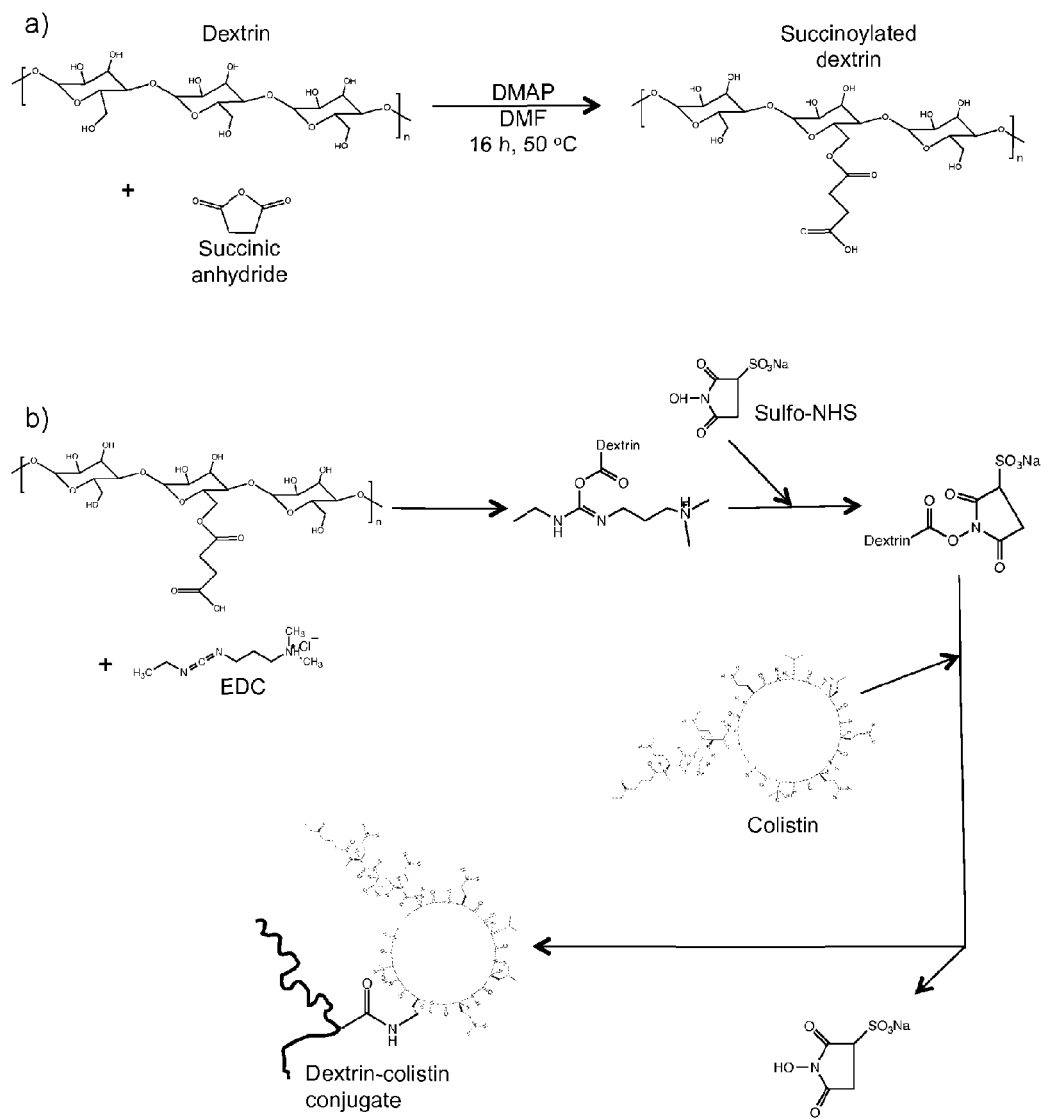
FIG. 2 shows the synthetic steps for the preparation of dextrin-colistin conjugates.
Figure 5:
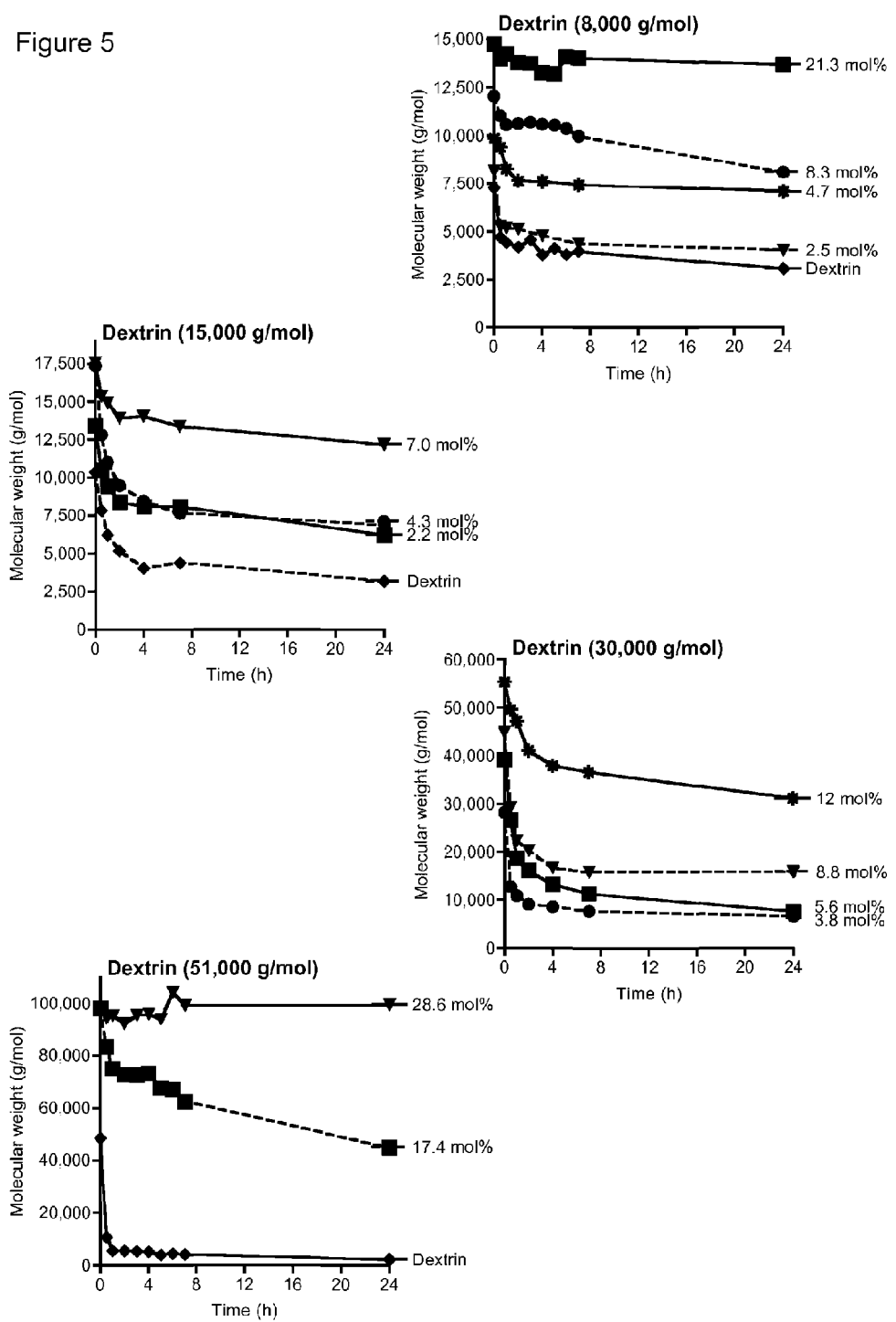
Figure 6A:
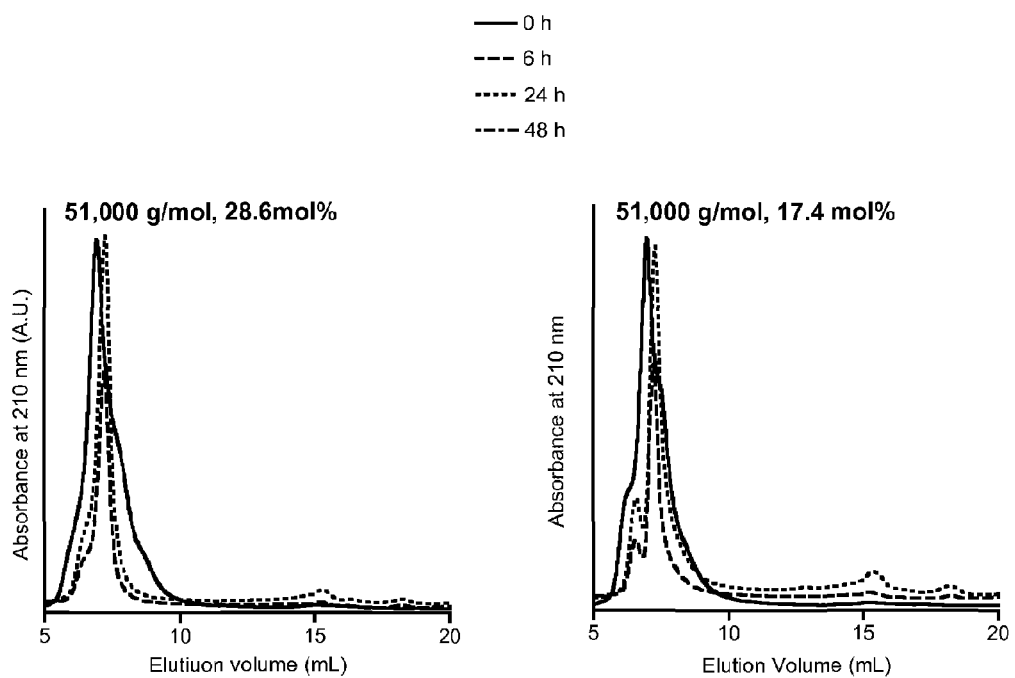
Figure 6B:
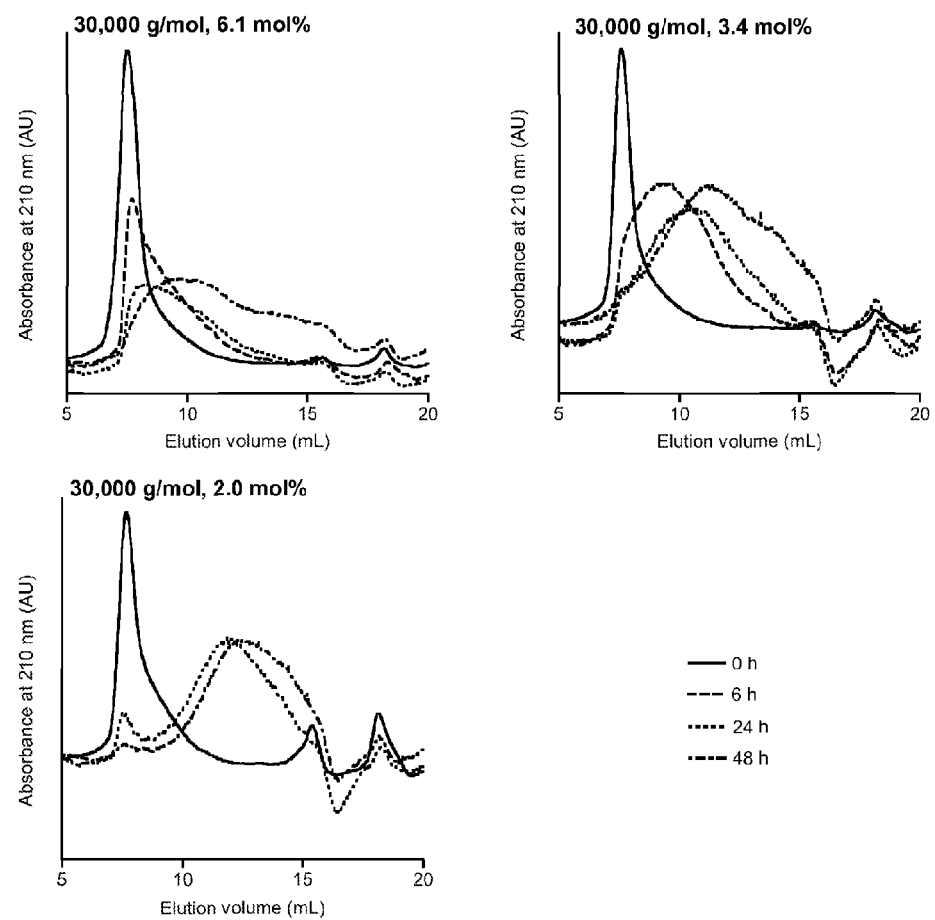
Figure 6C:
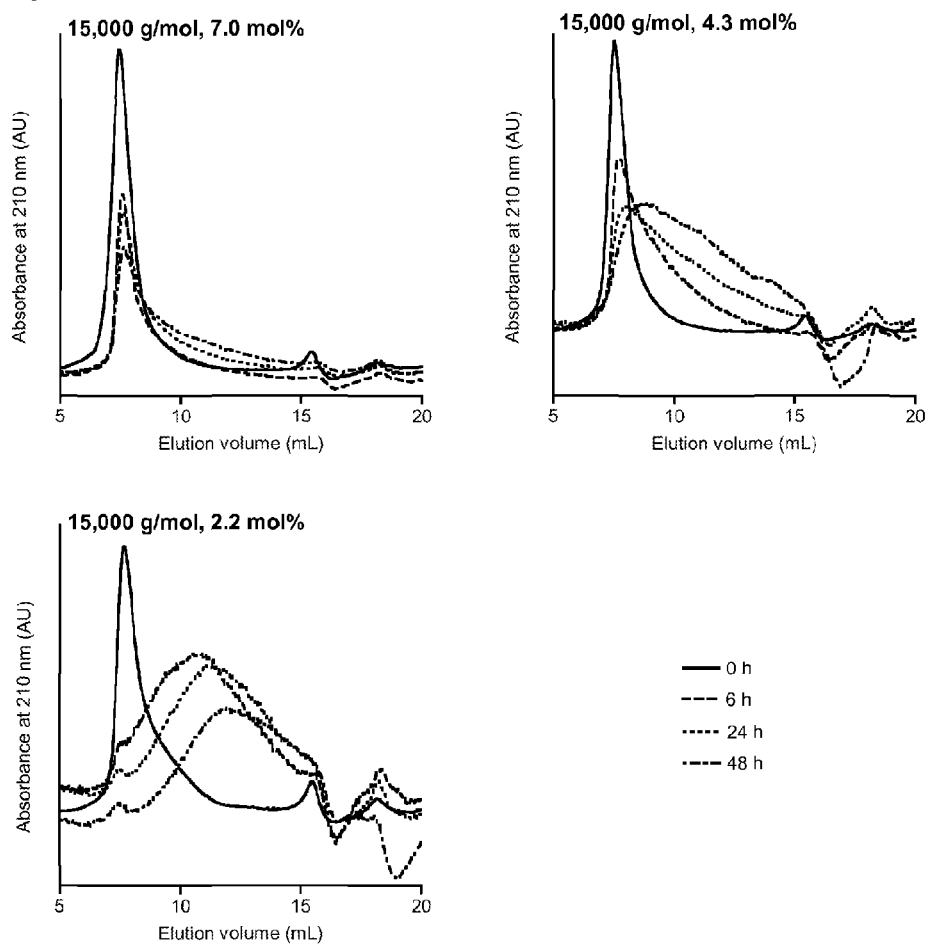

FIG. 5 demonstrates the effect of dextrin modification (by succinoylation) and molecular weight (8,000 g/mol; 15,000 g/mol; 30,000 g/mol and 51,000 g/mol) on degradation by amylase (100 IU/L in PBS);

FIG. 6(A-D) shows the elution of amylase-treated (100 IU/L in PBS) dextrin-colistin conjugates over time from a Superdex 75 FPLC column. Intact conjugates elute in the void volume (~7.5 mL) due to their larger size, while 'unmasked' colistin elutes later (~16 mL), facilitating the quantification of free colistin;

FIG. 7 illustrates the release of colistin from dextrin-colistin conjugates (measured by (a) FPLC and (b) GPC) during incubation with human amylase (100 IU/L in PBS) at 37° C. (in phosphate buffered saline (PBS), pH 7.4). Data in panel (a) is expressed as the percentage of total colistin;

FIG. 8 shows a comparison of the rate of colistin release from amylase-treated dextrin-colistin conjugates and CMS hydrolysis in PBS (measured by FPLC). Data is expressed as the percentage of total colistin;

FIG. 9 illustrates the stability of dextrin-colistin in water and PBS at pH 7.4 without enzymes (measured by FPLC). Data is expressed as the percentage of total colistin;

FIG. 10 shows the precipitation of LPS with colistin, CMS and dextrin-colistin conjugates (8,000 g/mol dextrin with 1 mol % succinoylation). Panel (a) shows concentration-dependent precipitation of LPS from *E. coli* (64-1000 μg/mL) with colistin (4 mg/mL) over 2 h. Panels (b) and (c) show precipitation of colistin, CMS, dextrin-colistin (+/−amylase) and succinoylated dextrin (4 mg/mL) with LPS from *E. coli* and *P. aeruginosa*, respectively (1000 μg/mL).

FIG. 11 shows the results of a conventional *Limulus* amoebocyte lysate (LAL) assay following incubation of LAL with LPS from *E. coli* (0-50 ng/mL) preincubated for 3 h at 37° C. with (a) colistin, CMS or pyrogen-free water, and (b) dextrin-colistin 8,000 g/mol dextrin with 1 mol % succinoylation (+/−amylase) at 4 μg/mL.

FIG. 12 shows how binding of colistin to dextrin reduces its toxicity towards HK2 kidney cells in an in vitro MTT assay (72 h incubation);

FIG. 13 shows the reduced toxicity of dextrin-colistin conjugates in HK2 kidney cells, compared to colistin and CMS, in an in vitro lactate dehydrogenase (LDH) assay (24 h incubation).

Table 1 shows the typical characteristics of batches of succinoylated dextrins;

Table 2 shows the typical characteristics of batches of dextrin-colistin conjugates;

Table 3 shows the antimicrobial activity of selected conjugates i.e 8,000 g/mol at 1.1 mol %, 2.5 mol % and 4.7 mol % succinoylation.

Materials & Methods

Materials.

Type 1 dextrin from corn (Mw~51,000 g/mol) was from ML laboratories (Keele, UK). Type I dextrin from corn (Mw~8,000 g/mol), dextrin from maize starch (Mw~30,000 g/mol), colistin, α-amylase from human saliva, N-hydroxysulfosuccinimide (sulfo-NHS), copper (II) sulphate pentahydrate 4% w/v solution, 3-(4,5-dimethylthiazol-2-yl)-2,5-diphenyl tetrazolium bromide (MTT), bicinchoninic acid solution (BCA), ethanolamine, ninhydrin, hydrindantin, lithium acetate dihydrate, acetic acid, dimethyl sulfoxide (DMSO), lipopolysaccharides from *Pseudomonas aeruginosa* 10, lipopolysaccharides from *Escherichia coli* 026:B6 (5) were all from Sigma-Aldrich (Poole, UK). Dextrin from potato starch (Mw~15,000 g/mol) was from Fluka (Gillingham, UK). 1-ethyl-3-(3-dimethylaminopropyl carbodiimide hydrochloride) (EDC) was from Pierce (Rockford, USA). Disodium hydrogen phosphate, potassium dihydrogen phosphate, sodium chloride, potassium chloride, 4-dimethylaminopyridine (DMAP) were from Fisher Scientific (Loughborough, UK). Toxinsensor chromogenic LAL endotoxin assay kit was from Jencons (Lutterworth, UK). Pullulan gel filtration standards (Mw=11,800-210,000 g/mol) were from Polymer Laboratories (Church Stretton, UK). Lactate dehydrogenase (LDH)-cytotoxicity assay kit was from abcam (Cambridge, UK). Phadebas® amylase assay kit was supplied by Magle Life Sciences (Lund, Sweden). Unless otherwise stated, all chemicals were of analytical grade. All solvents were of general reagent grade (unless stated) and were from Fisher Scientific (Loughborough, UK).

Human kidney proximal tubule cells (CRL-2190) were from ATCC (Manassas, USA). Cells were screened and found to be free of mycoplasma contamination before use. Foetal calf serum (FCS), Dulbecco's Modified Eagle Medium (DMEM) and 0.05% w/v trypsin-0.53 mM EDTA were obtained from Invitrogen Life Technologies (Paisley, UK).

Synthesis and Purification of Dextrin-Colistin Conjugates.

First, succinoylated dextrins (1-60 mol %) were synthesised (FIG. 2*a*). Briefly, with dextrin of Mw 8,000 g/mol, 5 mol % succinoylation was achieved as follows. Dextrin (1000 mg, $6.17\times10^{-3}$ mol) was dissolved in anhydrous DMF (10 mL) in a 50 mL round bottom flask. Succinic anhydride (61.7 mg, $6.17\times10^{4}$ mol) and DMAP (28.6 mg, $2.34\times10^{4}$ mol) were subsequently added and the reaction purged with nitrogen, sealed and left to stir at 50° C. for 18 h. Then, the reaction mixture was poured into vigorously stirring diethyl ether (250 mL) and stirred overnight. The ether was removed by filtration under vacuum and the residual solid was dissolved in minimal distilled water ($dH_2O$), poured into a dialysis membrane (molecular weight cut-off 2,000 g/mol) and dialysed against 4×5 L dH$_2$O. The resultant solution was freeze-dried to yield succinoylated dextrin. The degree of succinoylation was quantified by titration against a standard solution of NaOH (5×10$^{-4}$ M) with bromophenol blue as indicator, and the product was further characterized by FT-IR (Avatar 360 ESP spectrometer with EZ OMNIC ESP 5.2 software; Thermo Nicolet, Loughborough, UK) to confirm identity and by gel permeation chromatography (GPC) (TSK G4000PW$_{XL}$, and G3000 PW$_{XL}$ columns (Polymer Laboratories, Church Stretton, UK) in series, mobile phase PBS (pH 7.4), flow rate of 1 mL/min) to measure its approximate molecular weight and polydispersity (compared to pullulan standards). Samples for GPC were prepared in PBS (3 mg/mL) and the eluate was monitored using a differential refractometer (Gilson 153). PL Caliber Instrument software, version 7.0.4, from Polymer Laboratories (Church Stretton, UK) was used for data analysis. Succinoylated dextrins (1-30 mol % succinoylation) were then conjugated to colistin (FIG. 2b). Briefly, for 10 mol % succinoylated dextrin, succinoylated dextrin (200 mg, 1.11×10$^4$ mol COOH; 2.50×10$^{-5}$ mol dextrin) was dissolved under stirring in dH$_2$O (1 mL) in a 10 mL round-bottomed flask. To this, EDC (21.3 mg, 1.11×10$^{-4}$ mol) amd sulfo-NHS (24.1 mg, 1.11×10$^4$ mol) were added, and the mixture was left stirring for 30 min. Subsequently, colistin (35 mg, 2.50×10$^{-5}$ mol) dissolved in dH$_2$O (1 mL) was added, followed by NaOH (0.5 M) dropwise to raise the pH to ~8.0. The reaction mixture was left stirring for up to 18 h, typically for 2 h. The conjugate was then purified from the reaction mixture by fast protein liquid chromatography (FPLC) (ÄKTA FPLC; Amersham Pharmacia Biotech, UK) using a pre-packed Superdex 75 10/300 GL column with a UV detector and data analysis using Unicorn 4.0 software (Amersham Pharmacia Biotech, UK). Samples of the reaction mixture (0.5 mL) were injected into a 500 μL loop using PBS (pH 7.4), pH 7.4 at 0.5 mL/min as a mobile phase. Fractions (1 mL) were collected, desalted using Vivaspin tubes (5,000 g/mol cut-off) and assayed for protein content (BCA assay) before pooling fractions containing conjugate (typically fractions 6-13). The final conjugate was lyophilised and stored at −20° C.

Characterisation of Dextrin-Colistin Conjugates.

Dextrin-colistin was characterised by FPLC and GPC to assess purity and estimate molecular weight, and the total protein content of the conjugate was determined by the BCA assay using colistin standards.

The FPLC system described above for purification was used again for final conjugate characterisation. Samples (200 μL) were dissolved in PBS (pH 7.4) and injected into a 100 μL loop at 0.5 mL/min. The molecular weight was estimated using GPC relative to pullulan standards.

Ninhydrin Assay.

Prior to conjugation of polymer to protein, it was first important to determine the number of available amine groups in colistin for conjugation and how many amine groups were subsequently used for binding to dextrin.

First, a 4 M lithium acetate buffer solution was prepared by dissolving lithium acetate dihydrate (40.81 g) in 60 mL dH$_2$O. Sufficient acetic acid (glacial) was added until pH 5.2 was reached. The volume was made up to a final volume of 100 mL with dH$_2$O. Next, ninhydrin (0.2 g) and hydrindantin (0.03 g) were dissolved in 7.5 mL DMSO and 2.5 mL lithium acetate buffer. Buffered ninhydrin reagent (86 μL) was added to an equal quantity of sample/standard solution (1.5 mL eppendorf) and heated in a water bath at 100° C. for 15 min. The mixture was subsequently cooled to room temperature and 130 μL of 50% v/v ethanol was added. The solution was mixed before adding 200 μL of the final solution into wells of a 96-well plate. Spectrophotometric analysis was performed at 570 nm. Calibration of the assay was achieved using ethanolamine (0-0.1158 mM).

Degradation of Dextrin, Succinoylated Dextrin and Dextrin-Colistin Conjugates by Amylase.

To compare the rate of amylase degradation of dextrin, succinoylated dextrin and dextrin-colistin conjugates, solutions (3 mg/mL in PBS, pH 7.4) of each sample was prepared containing amylase (100 IU/L in PBS) and incubated at 37° C. for up to 48 h. At various time points, samples (300 μL) were taken, immediately snap frozen in liquid nitrogen to stop the reaction and then stored at −20° C. until analysis by GPC and FPLC (conjugates only). Prior to analysis, samples were placed in a water bath (100° C.) for 5 min to denature the enzyme activity of the amylase and stop polymer degradation. The supernatant was then analysed by GPC to determine the change in molecular weight over time and by FPLC to determine the change in free colistin over time.

Measurement of Antimicrobial Activity.

Antimicrobial activity was measured using broth microdilution in a minimum inhibitory concentration (MIC) assay according to the Clinical and Laboratory Standards Institute (formerly NCCLS; 2003, Methods for Dilution Antimicrobial Susceptibility Tests for Bacteria That Grow Aerobically, Approved Standard—Sixth Edition. M7A6. Clinical and Laboratory Standards Institute. Wayne, Pa.). Test organisms were suspended in Mueller Hinton cation adjusted broth (100 μL, 1-5×10$^4$ CFU/mL) and incubated in 96-well microtitre plates in serial two-fold dilutions of the test compounds.

The antimicrobial activity of dextrin-colistin was also determined following incubation of the conjugate with amylase. Dextrin-colistin conjugates (3 mg/mL colistin eq.) were first incubated with amylase (100 IU/L for up to 48 h at 37° C. in PBS buffer (pH 8.2)).

LPS Turbidity Assay

A turbidimetric assay technique was used in which the binding of LPS to colistin results in precipitation of aggregates and increased turbidity that can be measured spectrophotometrically at 625 nm.

LPS was dissolved in pre-warmed PBS buffer (0-1000 μg/mL, 37° C.) containing colistin, CMS, dextrin-colistin or unmasked dextrin-colistin (4 mg/mL, 200 μL per well) and added to the wells of a 96-well microtitre plate. Control samples contained only LPS dissolved in PBS. Plates were incubated at 37° C. throughout the experiment and absorbance was read at 625 nm at various timepoints (0, 15, 30, 60, 90, 120 min). Samples were assayed in triplicate and experiments were repeated once, and means of the results were calculated.

To study the effect of amylase on the activity of dextrin-colistin conjugates, dextrin-colistin conjugates (10 mg/mL) were first incubated with amylase (100 IU/L) for 6 h and 24 h at 37° C. in PBS (pH 8.2). The endotoxin binding activity assays were then followed as described above.

LAL Assay

A colorimetric assay technique was used in which the clotting reaction of *Limulus* amoebocyte lysate (LAL) in the presence of LPS was measured spectrophotometrically at 540 nm.

LPS was dissolved in pyrogen free water (0-50 ng/mL) containing colistin, CMS, dextrin-colistin or unmasked dextrin-colistin (4 μg/mL, 100 μL) in pyrogen-free vials. Control samples contained only LPS dissolved in pyrogen-free water. Solutions were mixed well and incubated at 37° C. for 3 h. Reconstituted LAL (100 μL) was then added and the solution mixed well before incubation at 37° C. for 45 min. Next, reconstituted substrate solution (100 µL) was added to each vial, mixed well and incubated for a further 6 min. Finally, the reaction was terminated by addition of reconstituted stop solution and colour stabilisers. Samples (100 µL) were pipetted into the wells of a 96-well microtitre plate (6 wells per sample) and absorption was read spectrophotometrically at 540 nm. The concentration of LPS producing 50% maximal absorption was taken as the $ED_{50}$.

To study the effect of amylase on the activity of dextrin-colistin conjugates, dextrin-colistin conjugates (0.5 mg/mL) were first incubated with amylase (100 IU/L) for 6 and 24 h at 37° C. in PBS (pH 8.2). The endotoxin binding activity assays were then followed as described above.

In Vito Toxicity Assay

MTT Assay

The MTT assay was used to assess cell viability (72 h incubation) in a human kidney (HK2) cell line. Cells were seeded into sterile 96-well microtitre plates ($1 \times 10^5$ cells/mL) in 0.1 mL/well of media (DMEM) containing FCS (10% v/v). They were allowed to adhere for 24 h. The medium was then removed and test compounds (0.2 µm filter-sterilized) were added to the cells. To study the effect of colistin, CMS, dextrin-colistin conjugate and succinoylated dextrin (8,000 g/mol, 1.1 mol % succinoylation) on cell viability, complete media (+FCS) was supplemented with a range of concentrations of each. To study the effect of 'unmasked' dextrin-colistin on cell viability, complete media (+FCS) was supplemented with a range of concentrations of conjugate and amylase (100 IU/L). After a further 67 h incubation, MTT (20 µL of a 5 mg/mL solution in PBS) was added to each well and the cells were incubated for a further 5 h. The medium was then removed and the precipitated formazan crystals solubilized by addition of optical grade DMSO (100 µL) over 30 min. Absorbance was measured at 540 nm using a microtitre plate reader. Cell viability was expressed as a percentage of the viability of untreated control cells. The $IC_{50}$ values were expressed as mean±SEM (n=18).

LDH Assay The LDH used to assess cell membrane damage (24 h incubation) in a HK2 cell line. Cells were seeded into sterile 96-well microtitre plates ($1 \times 10^5$ cells/mL) in 0.1 mL/well of media (DMEM) containing FCS (10% v/v). They were allowed to adhere for 24 h. The medium was then removed and test compounds (0.2 µm filter-sterilized) were added to the cells. To study the effect of colistin, CMS and dextrin-colistin conjugate on cell membrane integrity, complete media (+FCS) was supplemented with a range of concentrations of each. To study the effect of 'unmasked' dextrin-colistin on cell viability, complete media (+FCS) was supplemented with a range of concentrations of conjugate and amylase (100 IU/L). After 24 h, microtitre plates were centrifuged (600 g, 10 min) and the supernatant was transferred to a clean 96-well plate and stored at −20° C. until determination of LDH content. LDH content in the cell supernatant was determined using a commercial LDH-cytotoxicity assay kit (abcam) following the manufacturer's protocol. Absorbance was measured at 450 nm using a microtitre plate reader. The absorbance values were expressed as mean±SEM (n=6).

Results

Synthesis and Characterisation of Dextrin-Colistin Conjugates.

Figure 3:
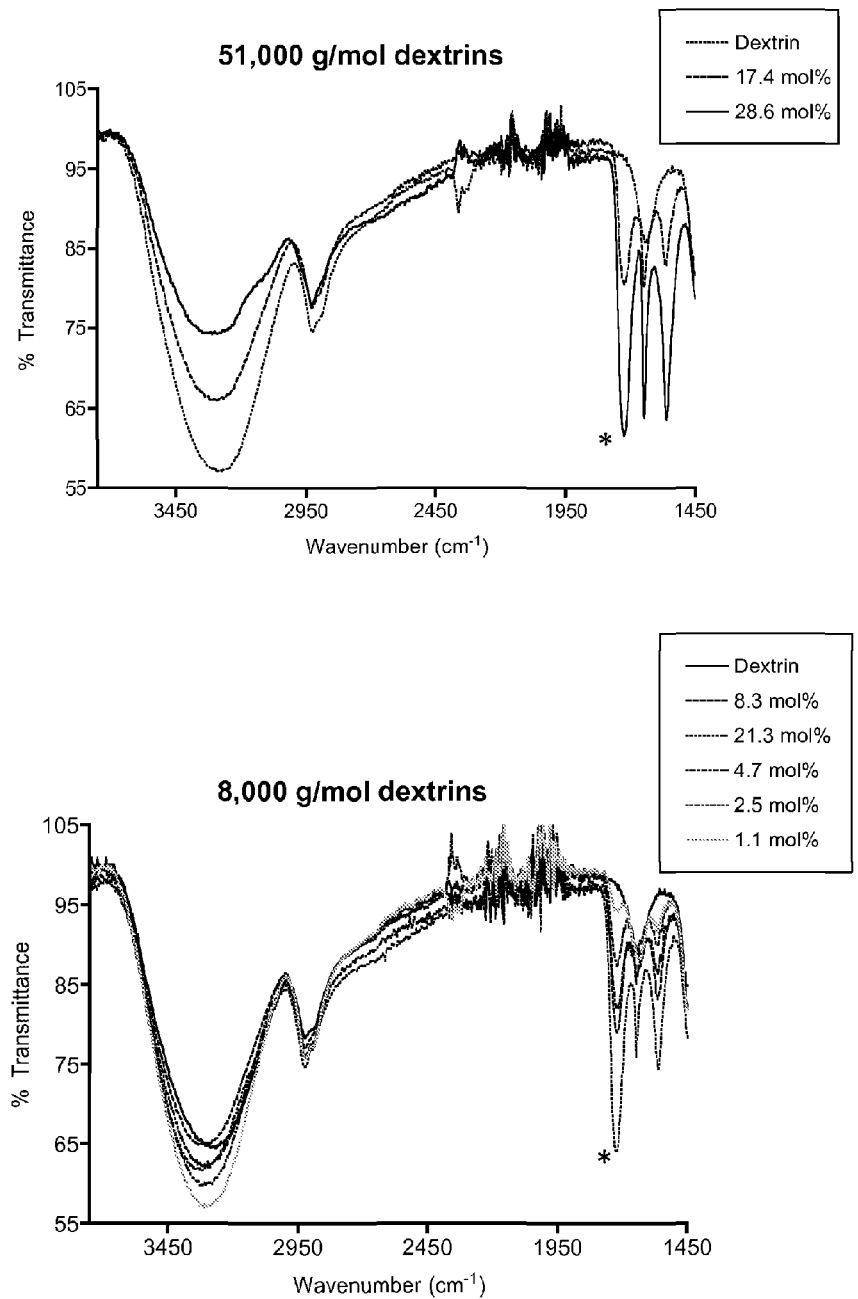
FIG. 3 shows the Fourier-transform infrared (FT-IR) spectrum of dextrin (51,000 g/mol and 8,000 g/mol) and succinoylated forms (17.4 mol %, 28.6 mol % at 51,000 g/mol; 8.3 mol %, 21.3 mol %, 4.7 mol %, 2.5 mol %, 1.1 mol % at 8,000 g/mol) of dextrins, illustrating the increase in peak intensity at 1720 $cm^{-1}$ (*) when succinoyl ester groups are incorporated into dextrin.

The characteristics of the library of succinoylated dextrins synthesised are summarised in Table 1. Succinoylated dextrin intermediates were synthesised having a degree of modification of 1-29 mol % and showed increased FT-IR signal strength of the ester peak (~1,720 cm$^{-1}$) relative to degree of modification (FIG. 3). This signifies the incorporation of ester groups into the dextrin i.e. succinoylation. Thus, signal increases as succinoylation is increased. GPC using pullulan standards suggested an increase in dextrin molecular weight following succinoylation with little change in polydispersity.

Figure 4:
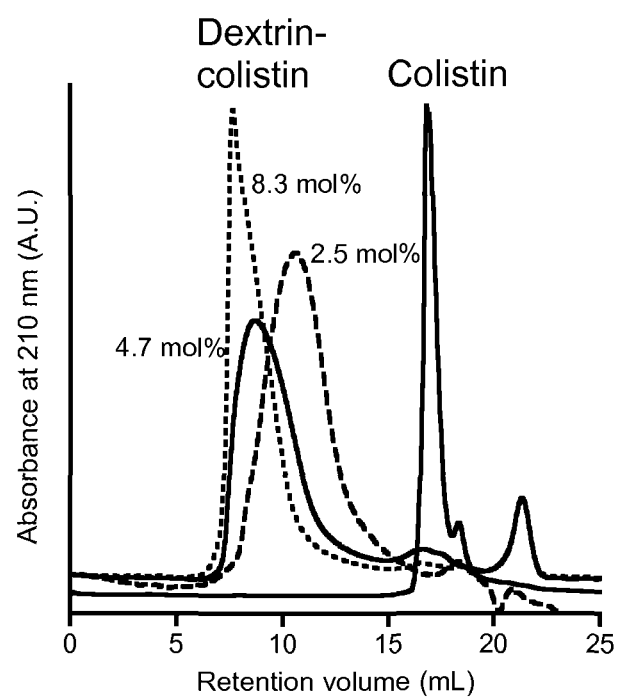
FIG. 4 illustrates the elution of dextrin-colistin conjugates (containing 8,000 g/mol dextrin at 8.3 mol %, 4.7 mol % and 2.5 mol % succinoylation) and free colistin from a Superdex 75 FPLC column. Conjugates elute in the void volume (~7.5 mL) due to their larger size than colistin, facilitating separation by FPLC.

Using this succinoylated dextrin intermediate a series of dextrin-colistin conjugates were prepared (Table 2). Typical FPLC elution profiles of the purified conjugates and free colistin are shown (FIG. 4). There was a good separation between bound and free colistin, with the conjugate typically eluting in the void volume of the column, thus enabling the separation of free and bound colistin. The protein content was 3-23% w/w. FPLC analysis confirmed the presence of a high molecular weight conjugate, however, the free colistin content was always <4%. The ninhydrin assay indicated that colistin has 4.8 $NH_2$ groups per molecule and that dextrin typically bound to ~3 of these groups in dextrin-colistin conjugates.

Degradation of Dextrin and Dextrin-Colistin Conjugate by Amylase.

GPC analysis of dextrin degradation by amylase revealed a decrease in molecular weight with time in a concentration-dependent manner (FIG. 5). While dextrin degraded rapidly ($t_{1/2}$<30 min) in the presence of amylase, chemical modification by succinoylation slowed the rate of degradation ($t_{1/2}$≥4 h).

Figure 7:
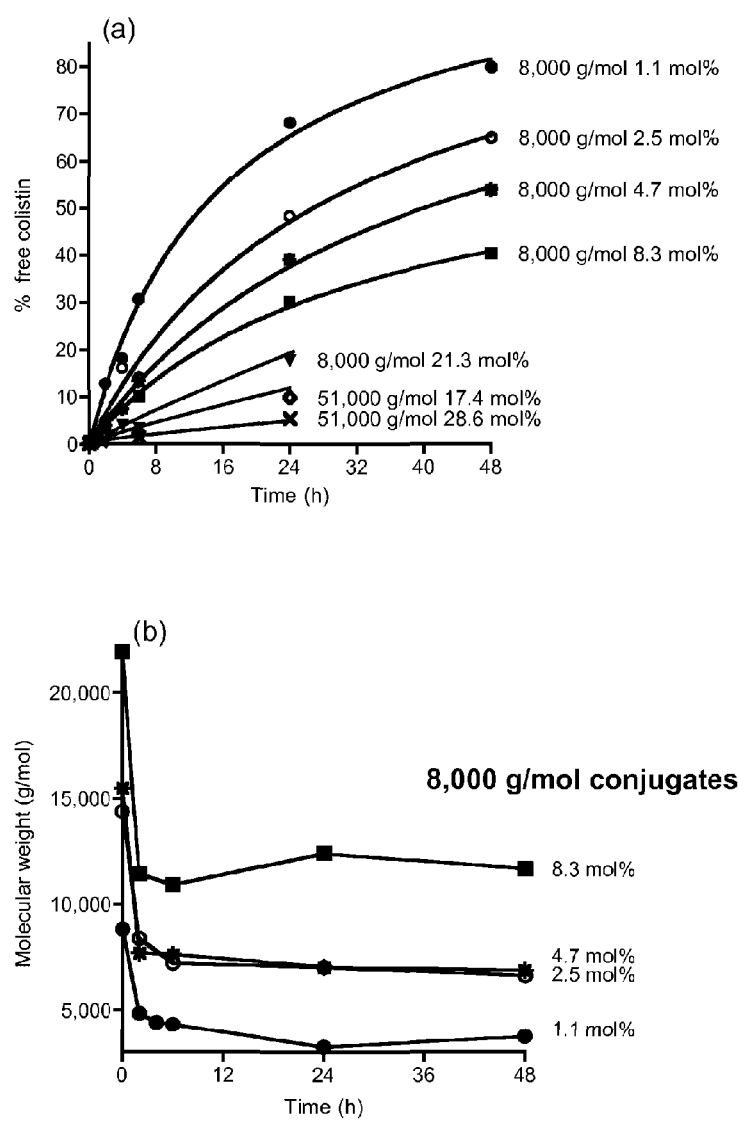
Figure 8:
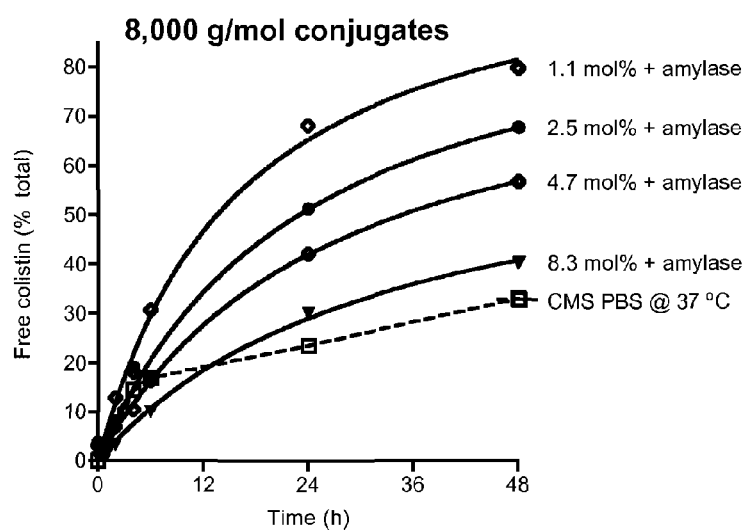

When degraded dextrin-colistin conjugates were analysed by FPLC, a peak corresponding to free colistin appeared (~16 mL), which increased in intensity with time (FIG. 6). In parallel, the peak corresponding to dextrin-colistin conjugate (~7.5 mL) decreased over the incubation timecourse. This corresponds to an increasing concentration of free colistin in parallel to reducing concentrations of dextrin-colistin conjugate-indicative of release of colistin from the conjugate due to amylase degradation of dextrin. In these experiments, dextrin-colistin conjugates containing low molecular weight dextrin (8,000 g/mol) with a low level of polymer modification (1.1 mol %) released the most free colistin (85%) after 48 h incubation (FIG. 7). Amylase-triggered dextrin-colistin conjugates synthesised using low molecular weight (8,000 g/mol) dextrin released more than twice as much free colistin within 48 h than the commercially available CMS (FIG. 8).

Measurement of Antimicrobial Activity.

Conjugation of dextrin effectively masked the antimicrobial activity of colistin in a panel of Gram-negative bacteria. However, incubation with amylase (at physiological concentrations) degraded the polymer and reinstated antimicrobial activity to varying degrees within 16 h (Table 3). Antimicrobial activity was greatest for conjugates containing low molecular weight dextrin (8,000 g/mol) with a low degree of succinoylation (1.1 mol %). Drug resistance often occurs when bacteria are exposed to sub-optimal concentrations of antibiotic, while high doses can cause unpleasant or harmful side effects. Masking of antibiotic activity in transit followed by efficient reinstatement of antibiotic activity after passive localisation at sites of infection and inflammation by the EPR effect provides an ideal means of optimising drug dosing to reduce the emergence of resistance.

Stability of Dextrin-Colistin and CMS In Vitro.

Figure 9:
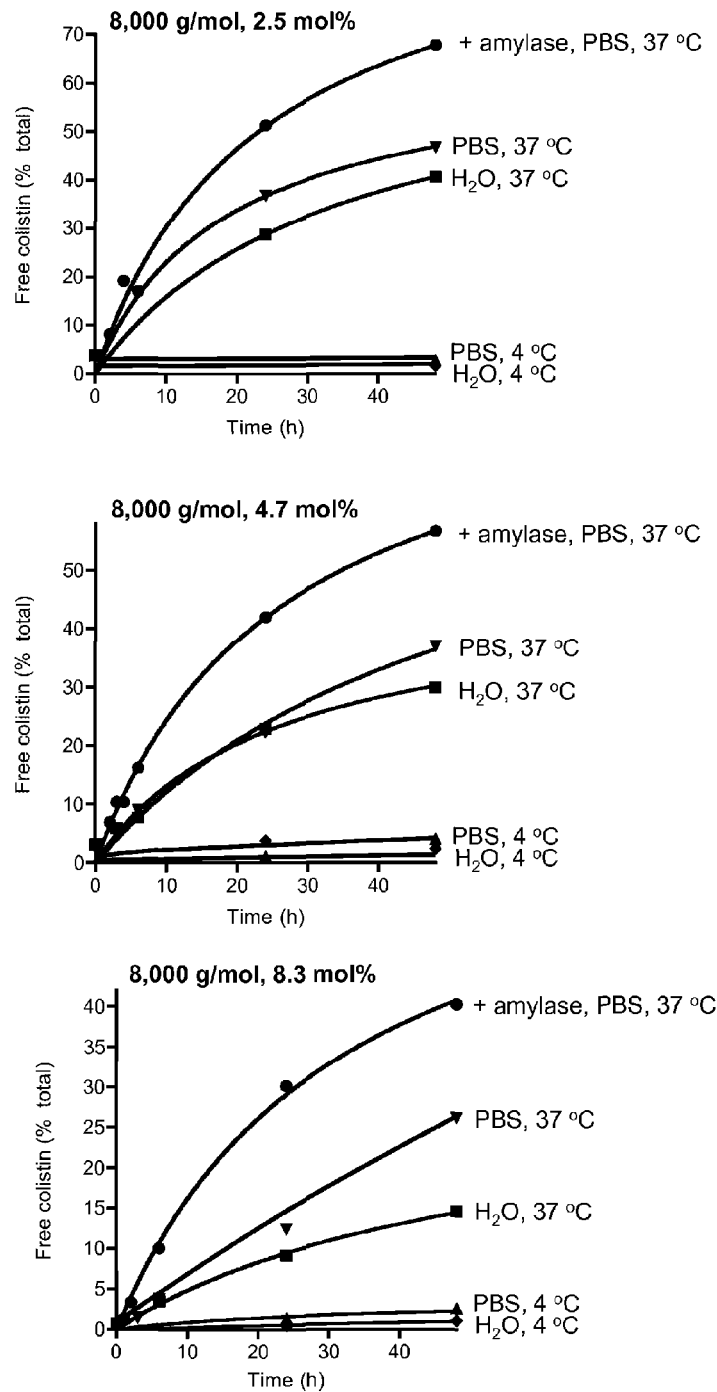

Dextrin-colistin conjugates (8,000 g/mol conjugates at 2.5, 4.7 and 8.3 mol %) were very stable in water and Phosphate buffered saline at 4° C. (FIG. 9). After 7 days, the percentage of liberated colistin was typically <5%. Dextrin-colistin conjugates were less stable in water at 37° C. in the absence of enzymes (in particular, amylase), and even more colistin was released in phosphate buffer at 37° C. in the absence of enzymes (in particular, amylase). Release of colistin by hydrolysis was also most significant for conjugates containing low degrees of succinoylation. This finding indicates that while amylase triggers significant release of free colistin from conjugates, drug may also be released at a slower rate in the absence of amylase. Some patients, such as those with cystic fibrosis, display reduced physiological levels of amylase. Enzyme-free liberation of drug would therefore be necessary for these patients. In all cases, the release of free colistin from dextrin-colistin conjugates was less than from amylase-activated conjugates.

LPS Binding/Endotoxin Neutralisation

LPS are characteristic components of the outer membrane of Gram-negative bacteria, which, when released, induce an inflammatory response and activation/secretion of pro-inflammatory cytokines, ultimately leading to sepsis and death. Colistin has a very high affinity for LPS, leading to the neutralisation of the endotoxins.

Turbidity Assay

Figure 10:
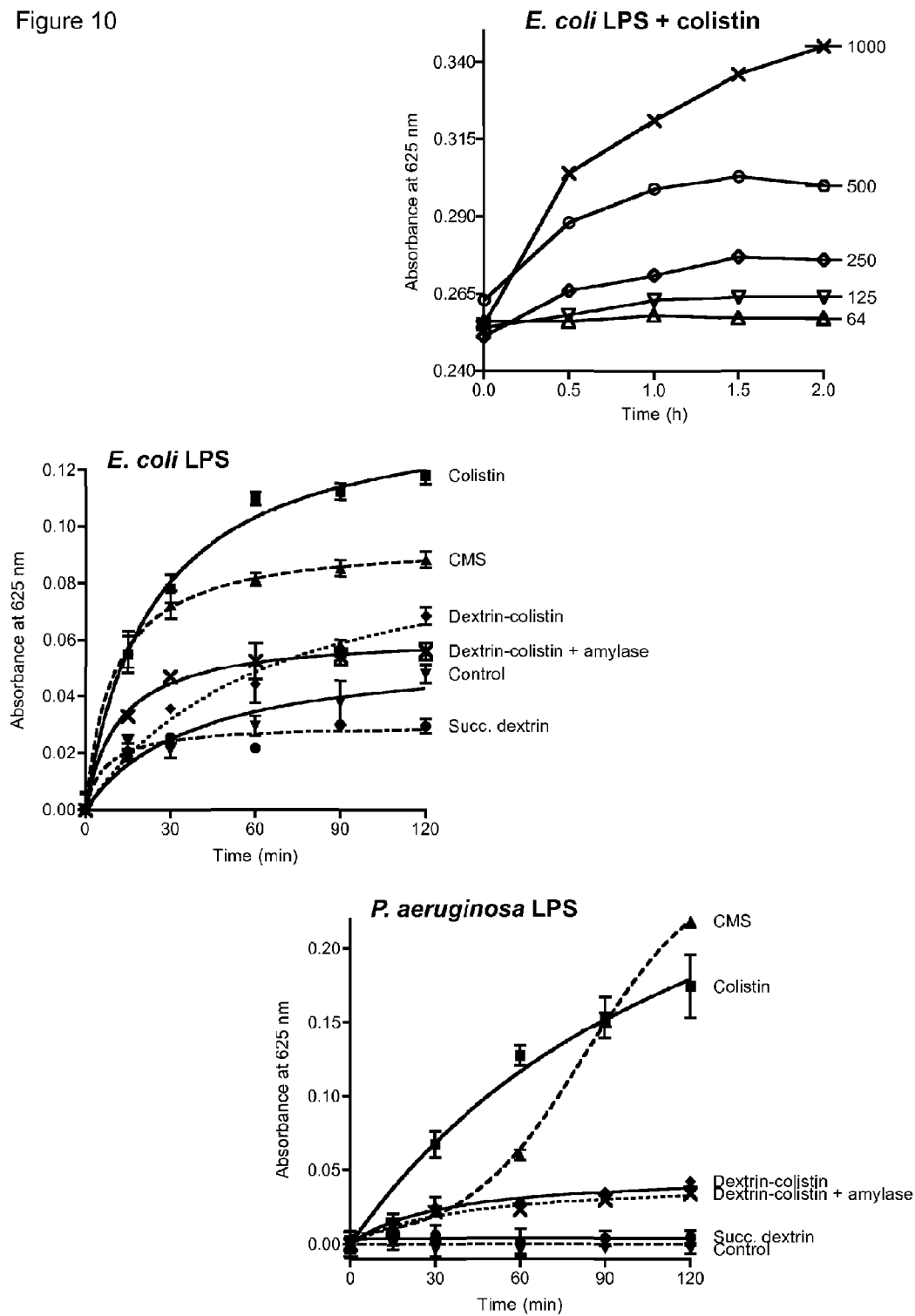

Increasing turbidity was used as a marker of LPS aggregate formation with colistin, CMS or dextrin-colistin conjugate. FIG. 10a (top graph) shows the aggregate formation of E. coli LPS at 64-1000 µg/mL with colistin at a constant 4 mg/mL, and demonstrates that increasing turbidity is clearly related to substrate concentration. When compared at equivalent colistin concentration, significant differences between the turbidity of colistin and CMS, dextrin-colistin (±amylase) or succinoylated dextrin/control were observed. It can be seen that LPS binding of the conjugate was reduced (to ~50% and ~20% for E. coli and P. aeruginosa LPS, respectively) compared to free colistin (FIGS. 10b,c—middle and lower graph). When dextrin-colistin was pre-incubated with amylase, turbidity did not significantly increase.

LAL Assay

Figure 11:
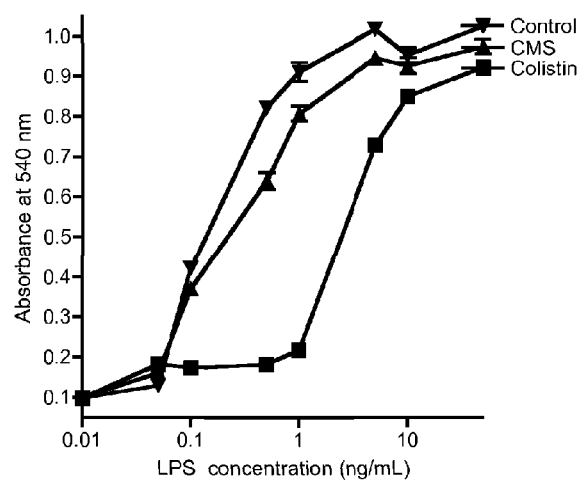
Figure 11:
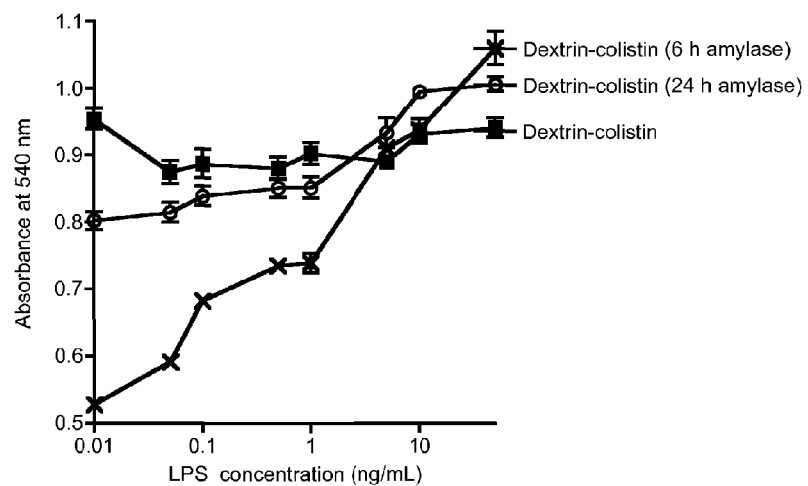

Colistin, and CMS to a lesser extent, was able to inhibit the cleavage of chromogenic substrate by E. coli LPS (FIG. 11a). Neutralisation of LPS by colistin required 20-fold more LPS to trigger Limulus amoebocyte lysate gelation compared to LPS in water, and was significantly greater than CMS.

Despite unmasked dextrin-colistin conjugate having considerable activity in the antimicrobial activity assays, all conjugate samples gelled Limulus amoebocyte lysate without the addition of LPS, indicative of endotoxin contamination (FIG. 11b). Nevertheless, at the lower concentrations of LPS, unmasked conjugate was capable of binding more LPS than masked conjugate and there was a trend for increasing endotoxin binding after unmasking by amylase (6 h>24 h>0 h).

In Vitro Toxicity Assay

Figure 12:
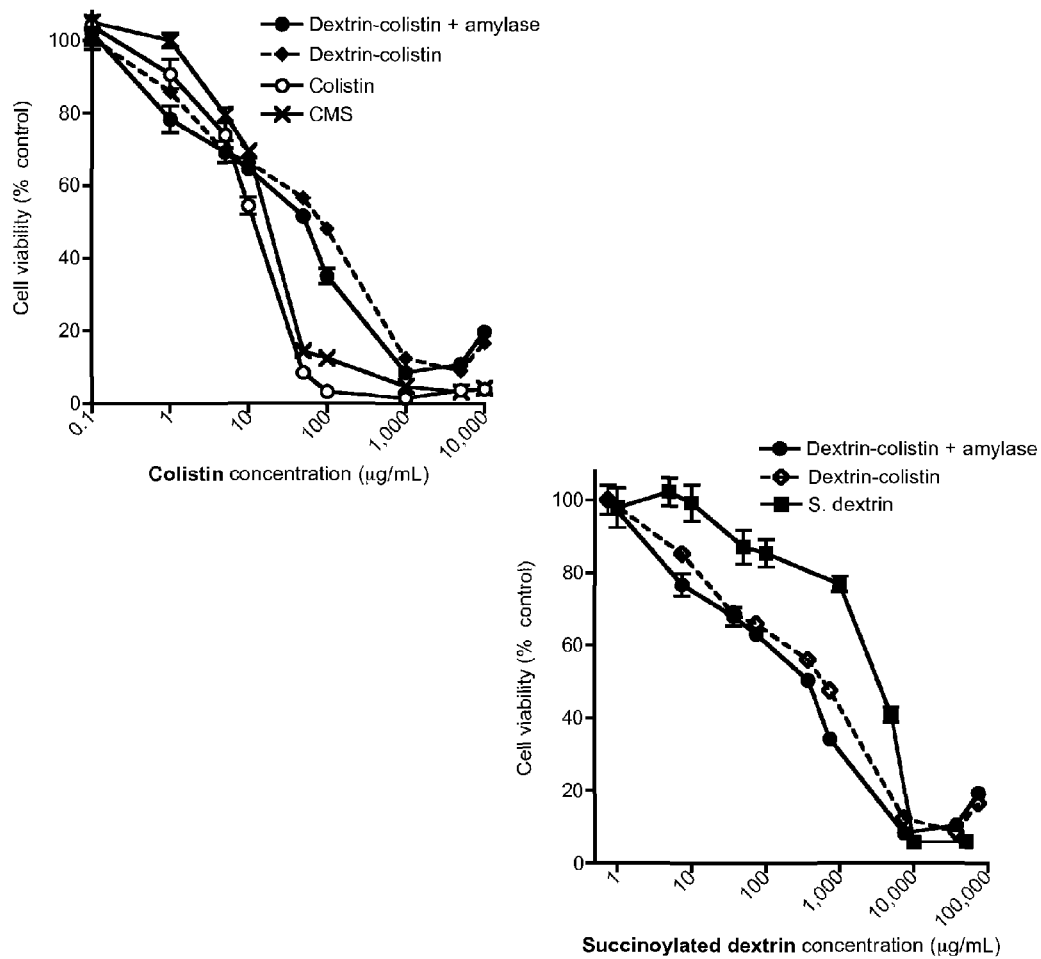
Figure 13:
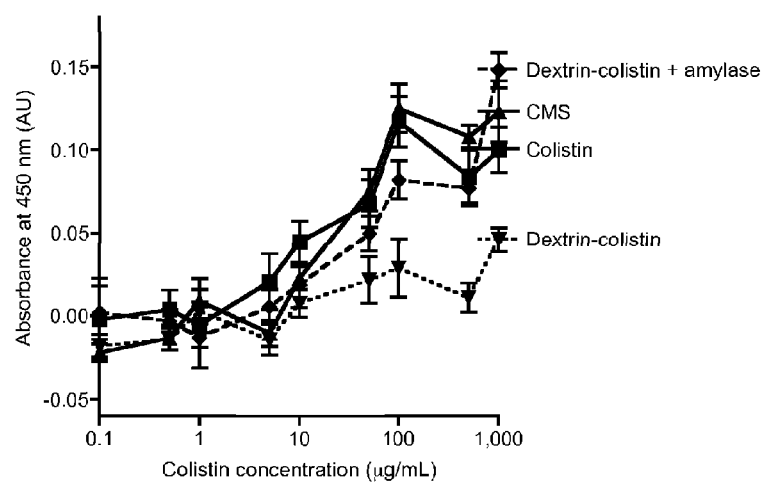

Colistin is inherently neuro- and nephrotoxic, which limits its use clinically. Here, we have assessed the in vitro toxicity of dextrin-colistin conjugates in a human kidney cell line. The dextrin-colistin conjugate was somewhat less toxic than free colistin and CMS in HK2 cells: the $IC_{50}$ values were 90, 20 and 25 µg/mL, respectively, from the MTT assay (FIG. 12). Although cell viability was slightly reduced in the presence of dextrin-colistin conjugate with amylase, toxicity was still 3-fold lower than free colistin. Similarly, the LDH assay in HK2 cells demonstrated that dextrin-colistin conjugate caused significantly less membrane damage than colistin or CMS (FIG. 13).

These findings demonstrate the reduced toxicity of dextrin-colistin conjugates, compared to free drug and the commercially available CMS.

CONCLUSION

Dextrin-antimicrobial conjugates, especially dextrin-colistin conjugates, are capable of delivering potentially toxic drugs for the treatment of Gram-negative infections. Release is triggered by physiological amylase, although drug is still liberated by hydrolysis in the absence of enzymes. This may be significant in the treatment of cystic fibrosis or chronic pancreatitis where enzymes may not be present. 'Unmasked' colistin from dextrin-colistin conjugates retains antimicrobial activity and may further benefit from accumulation within areas of infection and inflammation due to the EPR effect in vivo. Conjugates containing low molecular weight dextrin 5,000-15,000 g/mol (~8,000 g/mol) having a small degree of modification by succinoylation (~1.1 or 2.5 mol %) appear to be the most favourable systems for treating acute bacterial infections, while conjugates containing dextrin with a higher molecular weight 40,000-60,000 g/mol or degree of modification by succinoylation (>10 mol %) appear to be the most favourable systems for treating chronic infections.

TABLE 1

| Dextrin molecular weight (g/mol) | Degree of succinoylation (mol %) | Mw (g/mol) |
|---|---|---|
| 51,000 | 28.6 | 98,000 |
| 51,000 | 17.4 | 97,000 |
| 30,000 | 6.1 | 45,000 |
| 30,000 | 3.4 | 40,000 |
| 30,000 | 2.0 | 28,000 |
| 15,000 | 7.0 | 18,000 |
| 15,000 | 4.3 | 17,000 |
| 15,000 | 2.2 | 13,500 |
| 8,000 | 21.3 | 15,000 |
| 8,000 | 8.3 | 12,000 |
| 8,000 | 4.7 | 9,500 |
| 8,000 | 2.5 | 9,000 |
| 8,000 | 1.1 | 8,500 |

TABLE 2

| Conjugate characteristics | Molecular weight (g/mol) | Protein content (% w/w) | Molar ratio (dextrin:colistin) | Conjugated $NH_2$ per molecule* | Free protein (%) | % colistin release after 24 h |
|---|---|---|---|---|---|---|
| Colistin | 1,408 | 100 | — | 0 | 100 | 100 |
| CMS | 1,743 | 80.8 | — | 5 | <1 | 23.6 |
| 51,000 g/mol 28.6 mol % | 66,500 | 7.3 | 1:1.4 | 1.3 | 0.1 | 5.3 |
| 51,000 g/mol 17.4 mol % | 55,000 | 5.1 | 1:1 | 1.2 | 0.1 | 9.9 |
| 30,000 g/mol 6.1 mol % | 270,000 | 6.6 | 1:1.5 | 1.0 | 0.9 | ND |
| 30,000 g/mol 3.4 mol % | 140,000 | 3.0 | 1:0.7 | 1.4 | 1.3 | ND |
| 30,000 g/mol 2.0 mol % | 95,000 | 3.3 | 1:0.7 | 2.2 | 1.4 | ND |
| 15,000 g/mol 7.0 mol % | 180,000 | 14.5 | 1:1.8 | 1.4 | 2.8 | ND |

TABLE 2-continued

| Conjugate characteristics | Molecular weight (g/mol) | Protein content (% w/w) | Molar ratio (dextrin:colistin) | Conjugated NH$_2$ per molecule* | Free protein (%) | % colistin release after 24 h |
|---|---|---|---|---|---|---|
| 15,000 g/mol 4.3 mol % | 165,000 | 11.5 | 1:1.4 | 1.6 | 2.4 | ND |
| 15,000 g/mol 2.2 mol % | 35,000 | 10.6 | 1:1.3 | 1.4 | 2.9 | ND |
| 8,000 g/mol 21.3 mol % | 16,500 | 22.1 | 1:1.6 | ND | 0.8 | 17.7 |
| 8,000 g/mol 8.3 mol % | 17,000 | 21.6 | 1:1.6 | 3.5 | 0.8 | 30.2 |
| 8,000 g/mol 4.7 mol % | 15,500 | 22.2 | 1:1.6 | 3.0 | 2.0 | 39.1 |
| 8,000 g/mol 2.5 mol % | 14,500 | 17.0 | 1:1.2 | 3.2 | 2.7 | 48.4 |
| 8,000 g/mol 1.1 mol % | 9,000 | 10.1 | 1:0.6 | 3.3 | 3.7 | 68.2 |

* = usually 4.8 NH$_2$ per free colistin (ninhydrin assay),
ND = not determined

TABLE 3

| Bacterial species | 2 mol % | | | | 5 mol % | | | | 10 mol % | | | | Colistin | CMS |
|---|---|---|---|---|---|---|---|---|---|---|---|---|---|---|
| | 0 | 3 | 6 | 24 | 0 | 3 | 6 | 24 | 0 | 3 | 6 | 24 | 0 | 0 |
| Pseudomonas aeruginosa PA01 | 64 | 128 | 256 | 64 | 256 | 256 | 128 | 128 | 512 | 256 | 256 | 256 | 0.06 | 1 |
| Pseudomonas aeruginosa R22 PSA | 128 | 128 | 128 | 128 | 256 | 256 | 256 | 256 | >1024 | 1024 | 1024 | 1024 | 0.03 | 0.5 |
| Pseudomonas aeruginosa MDR 301 PSA | 512 | 512 | 512 | 512 | 1024 | 512 | 512 | 512 | >1024 | >1024 | >1024 | >1024 | 0.125 | 1 |
| Klebsiella pneumoniae KP05 506 | 4 | 8 | 16 | 16 | 512 | 64 | 32 | 64 | 1024 | 512 | 128 | 256 | 0.125 | 2 |
| Acinetobacter baumannii MDR ACB | 8 | 16 | 16 | 16 | 16 | 32 | 32 | 32 | 1024 | 256 | 128 | 256 | 0.125 | 4 |
| Escherichia coli AIM-1 | <1 | <1 | <1 | <1 | 16 | 32 | 32 | 32 | 1024 | 256 | 128 | 256 | 0.01 | 0.25 |
| Klebsiella pneumoniae IR25 | 8 | 16 | 16 | 16 | 32 | 16 | 8 | 16 | 64 | 64 | 128 | 256 | 0.03 | 2 |
| Providencia stuartii IR57 | 4 | 32 | 8 | 8 | <1 | <1 | <1 | <1 | 64 | 32 | 16 | 16 | 0.01 | 1 |
| Klebsiella pneumoniae K3 | 8 | 16 | 64 | 32 | 32 | 16 | 8 | 16 | 64 | 64 | 128 | 256 | 0.06 | 2 |
| Acinetobacter baumannii | 64 | 256 | 256 | 256 | 64 | 128 | 32 | 32 | 128 | 128 | 128 | 512 | 0.03 | 4 |
| Acinetobacter lwoffi | 128 | 128 | 64 | 64 | 32 | 32 | 16 | 128 | 512 | 256 | 256 | 256 | 0.25 | 4 |
| Escherichia coli 5702 | 4 | 8 | 8 | 2 | 64 | 32 | 64 | 32 | 128 | 128 | 64 | 64 | 0.03 | 1 |
| Klebsiella pneumoniae 5725 | 2 | 8 | 8 | 4 | 32 | 32 | 32 | 64 | 128 | 64 | 64 | 128 | 0.03 | 1 |
| Acinetobacter baumannii 7789 | 8 | 16 | 16 | 8 | >1024 | 1024 | 1024 | 1024 | >1024 | >1024 | >1024 | >1024 | 0.03 | 2 |
| Acinetobacter lwoffi 8065 | 8 | 8 | 8 | 4 | 64 | 64 | 32 | 32 | 512 | 256 | 128 | 128 | ND | ND |
| Acinetobacter haemolyticus 1554 | >1024 | 1024 | 512 | 512 | 256 | 128 | 128 | 64 | 1024 | 512 | 256 | 256 | 4 | 8 |
| Acinetobacter lwoffi 6056 | 32 | 32 | 16 | 16 | 4 | 4 | 4 | 4 | 64 | 32 | 16 | 128 | 0.03 | 2 |
| Escherichia coli 7273 | 4 | 32 | 16 | 8 | 64 | 32 | 32 | 16 | 512 | 256 | 256 | 128 | <0.5 | 2 |
| Pseudomonas aeruginosa mucoid strain | 128 | 64 | 32 | 32 | ND | ND | ND | ND | ND | ND | ND | ND | 0.01 | 1 |
| Pseudomonas aeruginosa mucoid strain | 64 | 32 | 64 | 32 | ND | ND | ND | ND | ND | ND | ND | ND | 0.008 | 0.25 |

ND = not determined

The invention claimed is:

1. An anti-microbial peptide (AMP) polymer conjugate comprising colistin and a dextrin polymer wherein said dextrin polymer has a molecular weight between 5,000-15,000 g/mol and is modified by the addition of succinyl pendant groups to provide 0.5-10 mol % succinoylation which increase the stability of the conjugate and so delays its degradation thereby slowing the rate at which the AMP is released.

2. The conjugate according to claim 1 wherein said molecular weight is 8,000 g/mol.

3. The conjugate according to claim 1 wherein said colistin is in its free drug form.

4. The conjugate according to claim 3 wherein the dextrin to colistin conjugates typically contain approximately 3 amide bonds per colistin molecule.

5. The conjugate according to claim 3 wherein the molar ratio of dextrin to colistin is between 1:0.6 and 1:1.8.

6. The conjugate according to claim 1 wherein said modified dextrin is further modified by the addition of positively charged groups, neutral groups or negatively charged groups.

7. The conjugate according to claim 1 wherein said succinoylation is 0.5, 0.6, 0.7, 0.8, 0.9, 1.0, 1, 1.1, 2, 2.2, 2.5, 3, 3.4, 4, 4.7, 5, 6, 6.1, 7, 8, 8.3, 9, or 10%.

8. A pharmaceutical composition or formulation comprising the AMP polymer conjugate according to claim 1.

9. The pharmaceutical composition or formulation according to claim 8 wherein said composition is formulated for medical or veterinary use.

10. A method of treating a mammal suffering from a Gram-negative bacterial infection comprising administering to said mammal an effective amount of the conjugate according to claim 1 or the composition according to claim 8.

11. A method of treating a mammal suffering from sepsis comprising administering to said mammal an effective amount of the conjugate according to claim 1 or composition according to claim 8.

12. The method according to claim 10 wherein said mammal is human, equine, canine, feline, porcine, or any other domestic or agricultural species.

13. The method according to claim 11 wherein said mammal is human, equine, canine, feline, porcine, or any other domestic or agricultural species.

14. A method of manufacturing an anti-microbial peptide (AMP) polymer conjugate comprising:
 a) dissolving dextrin succinoylated between 0.5-10 mol % in a preparatory solvent;
 b) dissolving colistin in a preparatory solvent;
 c) adding the two solvents together and, optionally, at the same time, or subsequently, raising the pH; allowing the reaction mixture to react; and
 d) separating the conjugate from the reaction mixture.

15. The method according to claim 14 wherein said pH is raised to 8 or thereabouts.

16. The method according to claim 14 wherein the reaction mixture is left for up to 2 h.

17. A combination therapeutic, comprising the conjugate according to claim 1 or composition according to claim 8 and at least one other therapeutic agent.

* * * * *